United States Patent [19]

Rosenstiel et al.

[11] Patent Number: 4,824,367
[45] Date of Patent: Apr. 25, 1989

[54] DENTAL DRILL ALIGNMENT INDICATOR

[75] Inventors: Stephen F. Rosenstiel, Worthington, Ohio; Edwin R. I. Deane, London, England

[73] Assignee: National Research Development Corporation, London, England

[21] Appl. No.: 920,000

[22] Filed: Oct. 17, 1986

[30] Foreign Application Priority Data

Oct. 17, 1985 [GB] United Kingdom ................ 8525625

[51] Int. Cl.$^4$ .............................................. A61C 3/00
[52] U.S. Cl. ........................................ 433/75; 433/76; 433/27
[58] Field of Search ....................... 433/75, 76, 27, 114

[56] References Cited

U.S. PATENT DOCUMENTS

| | | | |
|---|---|---|---|
| 3,218,624 | 11/1965 | Zane | 433/75 |
| 3,462,842 | 8/1969 | Greenberg et al. | 433/27 |
| 3,839,797 | 10/1974 | Randolph | 433/27 |
| 3,863,067 | 2/1975 | Gooley | 250/231 R |

FOREIGN PATENT DOCUMENTS

| | | |
|---|---|---|
| 1542632 | 1/1979 | United Kingdom . |
| 2102570A | 2/1981 | United Kingdom . |
| 2145817A | 5/1985 | United Kingdom . |

OTHER PUBLICATIONS

"The Convergence Angle in Teeth Prepared for Artificial Crowns" Prof. Silness, 1978.
"The Parallelo-Facere: a Parallel Drilling Machine . . . ", Wm. Solle.
"Machine-Controlled Tooth Preparation", Dr. Jermyn
"Machine-Controlled Tooth Preparation-Part II"-Dr. Jermyn.
"An Intraoral Paralleling Instrument" Dr. Kopsiaftis.
"A New Parallelometer" Antonio de Rezende.
"A Paralleling Instrument for the Guidance of Pin . . . " Goran Karlstrom, L.D.S.
"A New Paralleling Instrument, Parmax II, . . . " Dr. Goransson and Ake Parmlid, L.D.S.
"Instrumentation for Solving Abutment Parallelism . . . " Dr. Gold.
"The Parallelometer Mirror", Bottger.
"The Guide Pin Technique for Paralleling . . . " O'Meeghan and Dr. Behrend.
"Paralleling in Conservative Dentistry" Dr. Thompson.
"Position Finder for Parallelism", Drs. Gamer and Zusman.

Primary Examiner—Robert Peshock
Assistant Examiner—Adriene J. Lepiane
Attorney, Agent, or Firm—Cushman, Darby & Cushman

[57] ABSTRACT

In dental surgery when a tooth is to be crowned, the tooth has to be prepared by cutting a taper. It has been found that for the successful mounting of a crown the taper must be much more exactly prepared than is possible using currently available equipment. The present invention allows the initial position of the axis of a cutter to be related by means of electronic "spirit levels" to a selected axis. Deviation from this axis by more than a predetermined amount is indicated by light sources which can be seen regardless of the position of a handpiece holding the cutter. By means of a code these light sources indicate how the dentist must move the cutter to return to the correct axis.

6 Claims, 5 Drawing Sheets

DENTAL DRILL ALIGNMENT INDICATOR

BACKGROUND OF THE INVENTION

The present invention relates to methods and apparatus for use by a dental practitioner to indicate when the axis of a dental bur or stone attached to a dental handpiece which the practitioner guides deviates from a required angular alignment.

Cast metal or porcelain crowns and inlays are restorations that are frequently needed for extensively damaged teeth. They are also used as retainers for fixed partial dentures (bridges). Each restoration is made in a dental laboratory on an exact model of a tooth which has been prepared for the restoration by a dentist. Once constructed, the restoration is returned to the dentist and cemented into place. Of critical importance to the success of the restoration is the convergence angle (that is the angle between opposing faces) or taper of the tooth preparation. If the walls of a tooth prepared for a crown converge towards the root of the tooth (negative taper or undercut) the restoration cannot be seated as it is "locked out". However, if too great a taper is given to the preparation, the appliance may become dislodged during function. This is because a truly adhesive dental cement is not yet available and crowns are retained by a friction developed by the cement between the prepared tooth and the internal surface of the restoration. The relationship between convergence angle and retention has been studied experimentally and is hyperbolic in nature, with half the retention lost as the taper increases from 5° to 10°. There is very little retention over 20°. Because of this most dental textbooks recommended a taper of around 6°, this being said to be the least practical taper without the risk of undercuts. The desired taper is imparted either by attempting to hold a rotary cutter with the desired taper at a constant angle to the tooth, or by varying the angle of the handpiece whilst using a cylindrical cutter.

At present most dental practitioners have great difficulty in realizing this measure of accuracy with the freehand techniques used at present. Ohm and Silness ("The convergence angle in teeth prepared for artificial crowns". J. Oral Rehabil. 5, 371 (1978)) measured the convergence angle of dies sent by dental practitioners to commercial laboratories and concluded that most preparation fell into the range of 12° to 37° rather than the desired 6°. The problem has been confirmed by other studies both in the UK and the USA. These studies concluded that the tooth preparations were commonly found to contain undercuts, overtapered surfaces and lack of a precisely defined path of insertion and that practitioners hardly ever reached the ideal (taper) described in the literature.

Not only is achieving a satisfactory taper by visual means along extremely difficult but assessment of the taper has been shown to be also very difficult. This may account for the observation that lack of retention is the second most common cause of failure of crowns and fixed partial dentures, caries being the most common.

A number of paralleling devices are known but none has been very successful. Some instruments work by temporarily fixing the dental handpiece in relationship to the teeth, movement being limited by a linked parallelogram device. In practice they have proved awkward and time consuming to align and assemble, as well as uncomfortable and intimidating to the patient.

Another group of devices is aimed at helping the dentist align the dental handpiece or at helping the assessment of the tooth preparation. One such device consists of a mirror scribed with parallel lines, another a laboratory made plastic base plate with parallel rods and another of a spirit level attached to the dental handpiece. These devices have the advantage that they do not interfere with the normal operating of the handpiece, but they are of limited value due to difficulties in feeding back the information to the dentist. For example, it is difficult to monitor the spirit level device while concentrating on the surgical procedure.

SUMMARY OF THE INVENTION

According to a first aspect of the present invention there is provided a parallel alignment indicator for a dental handpiece, comprising angle-indicator means for generating angle signals representative of angular orientation of the axis of a rotary cutter held, in operation, by a dental handpiece, setting means for setting reference signals representing the position of a selected axis, and warning means arranged to generate a warning when the relationship between the angle signals and the reference signals falls outside predetermined limits.

The dentist is able to prepare teeth while receiving information on inclination of the cutter without having his concentration upset momentarily by looking elsewhere for this information. A further advantage of the invention is that the patient can be arranged comfortably both from the dentists point of view and the patient's for working on a particular tooth or teeth. The handpiece can be brought into position to start cutting and then the selected axis established. From then on any deviation from parallel with the original cutter and handpiece position by more than a preset amount is indicated.

The angle signals may be representative of deviation from a reference axis and the setting means may include storage means for storing the angle signals when the handpiece has been positioned in a chosen position related to the selected axis, the warning means then including means for comparing the current angle signals with signals derived from the stored signals and a predetermined threshold signal.

The setting means may include means for adjusting the position of the angle-indicator means relative to the handpiece when the latter is in the chosen position to set the stored angle signals approximately to a chosen value. The reference signals may have zero value if the position of the angle indicator means is appropriately set when the handpiece is in the chosen position.

The alignment indicator may be attached to, or integral with, a dental handpiece.

The means for providing a warning may comprise a plurality of light sources which can be, or are, fixed to the handpiece so that wherever the handpiece is in the patient's mouth the dentist can see sufficient sources to observe a coded signal specifying both when the cutter is tilted by more than a certain amount with respect to the selected axis and also the direction of the tilt.

According to a second aspect of the present invention there is provided an alignment indicator comprising means for providing a signal representative of deviation from an alignment required in cutting and means for providing a warning when the said signal falls outside a required value range indicating satisfactory alignment, any visual warning preferably being, in operation, given within the field of view of an operator controlling cutting when the operator is in a convenient position to control cutting.

The invention also includes methods corresponding to the alignment indicators of the invention mentioned above.

BRIEF DESCRIPTION OF THE DRAWINGS

Certain embodiments of the invention will now be described by way of example with reference to the accompanying drawings, in which.

DETAILED DESCRIPTION OF THE PREFERRED EMBODIMENT

Figure 1A:
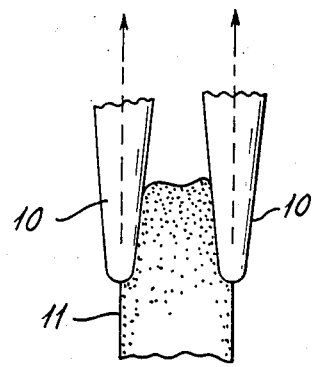
FIGS. 1a and 1b illustrate tooth preparation for crowning.
Figure 1B:
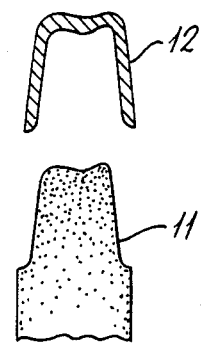

Preparation of a tooth for crowning is first described to enable operation of the invention to be appreciated. In FIG. 1 a rotary cutter 10 in the form of a dental bur or stone is shown in two positions: to the left and right of a tooth 11. The cutter is mounted in a dental handpiece (not shown in FIG. 1) and has an abrasive surface in the form of a cone. If the longitudinal axis of this cutter is maintained parallel to the axis of the tooth, the conical surface ensures a taper of the required six degrees as shown in FIG. 1b. A crown 12 can then be cemented over the tooth and will be held firmly in position. The axis of a tooth is indeterminate but as long as the cutter axis is held parallel to a selected axis which is approximately aligned with the tooth axis, the crown 12 which is made from a casting of the tooth will fit reliably because the taper all round the tooth is at six degrees to the selected axis.

Figure 2A:
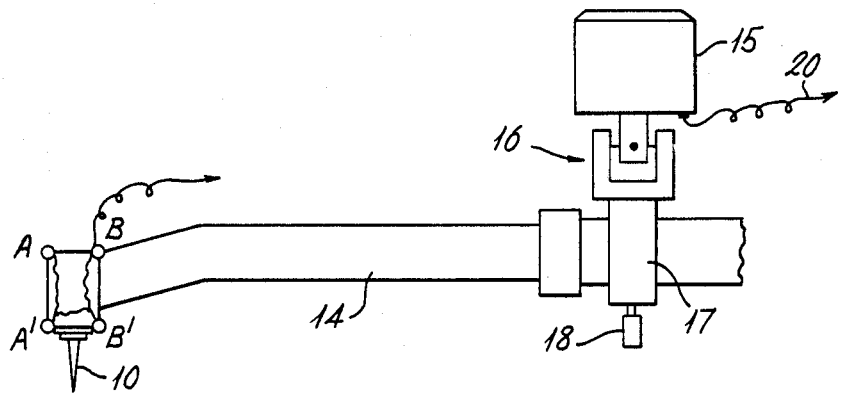
FIGS. 2a and 2b are side and plan views of a dental handpiece carrying sensor means and tilt indicators employed in an alignment indicator according to the invention.
Figure 2B:
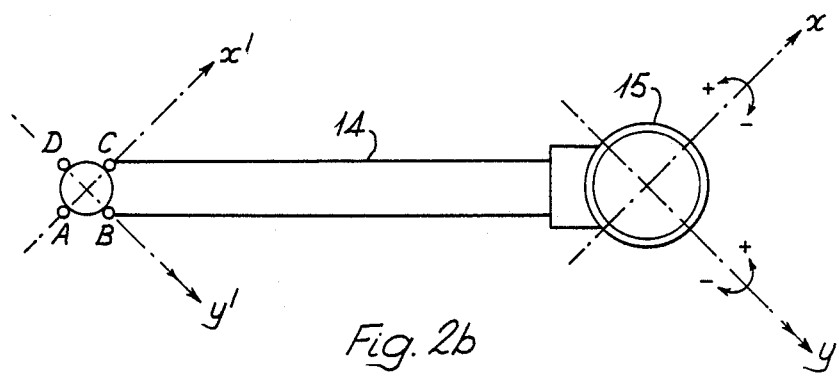

In FIGS. 2a and 2b a dental handpiece 14 holds the cutter 10. Eight light emitting diodes (LEDs) A,A', B,B', C,C' and D,D' are positioned at the cutter end of the handpiece so that wherever the handpiece is in the mouth enough of the LEDs can be seen to provide a code showing when the axis of the cutter 10 departs from being parallel with the selected axis by more than a specified amount.

Two electronic "spirit levels" which sense in orthogonal directions are located in the housing 15 which is mounted by means of a stiff movable two axis joint 16 on the handpiece 14 by means of a collar 17 and a locknut 18.

When the dentist intends to prepare a tooth, he first holds the handpiece approximately at the angle which he intends to operate, with the cutter 10 either above or below the handpiece for operating on teeth in the upper or lower jaw respectively. He then uses the locknut 18 to swivel the housing 15 so that its axis is approximately vertical. Next the cutter is put into the mouth adjacent the tooth to be prepared and held in the position judged to be correct for the start of cutting. At this time the joint 16 is used to make any further adjustments necessary to ensure that the axis of the housing 15 is approximately vertical and a footswitch is operated to set the selected axis. Signals from the spirit levels by way of connections 20 indicate rotation of the handpiece from the initial angular orientation about x and y axes as shown in FIG. 2b and these signals correspond to rotation of the axis of the cutter 10 about axes x' and y' so that any departure from parallel with the selected axis is indicated by the signals carried by the connections 20.

In the code used to indicate tilt, the LEDs are switched as follows:

| Direction of tilt | A,A' | B,B' | C,C' | D,D' |
|---|---|---|---|---|
| LOWER jaw orientation | | | | |
| +x | O | I | O | F |
| −x | O | F | O | I |
| +y | I | O | F | O |
| −y | F | O | I | O |
| UPPER jaw orientation | | | | |
| +x | I | O | F | O |
| −x | F | O | I | O |
| +y | O | I | O | F |
| −y | O | F | O | I |

I = ON
O = OFF
F = FLASHING

Wherever the cutter 10 is in the mouth at least one of the LEDs A, A', C, C' can be seen together with at least one of the LEDs B, B', D, D' and, as is apparent from the above code, these LEDs are sufficient to indicate tilt above a threshold and tilt direction.

In use the dentist simply has to tilt the tip of the cutter towards an LED which is flashing and tilt the tip away from an LED which is constantly on.

Figure 3:
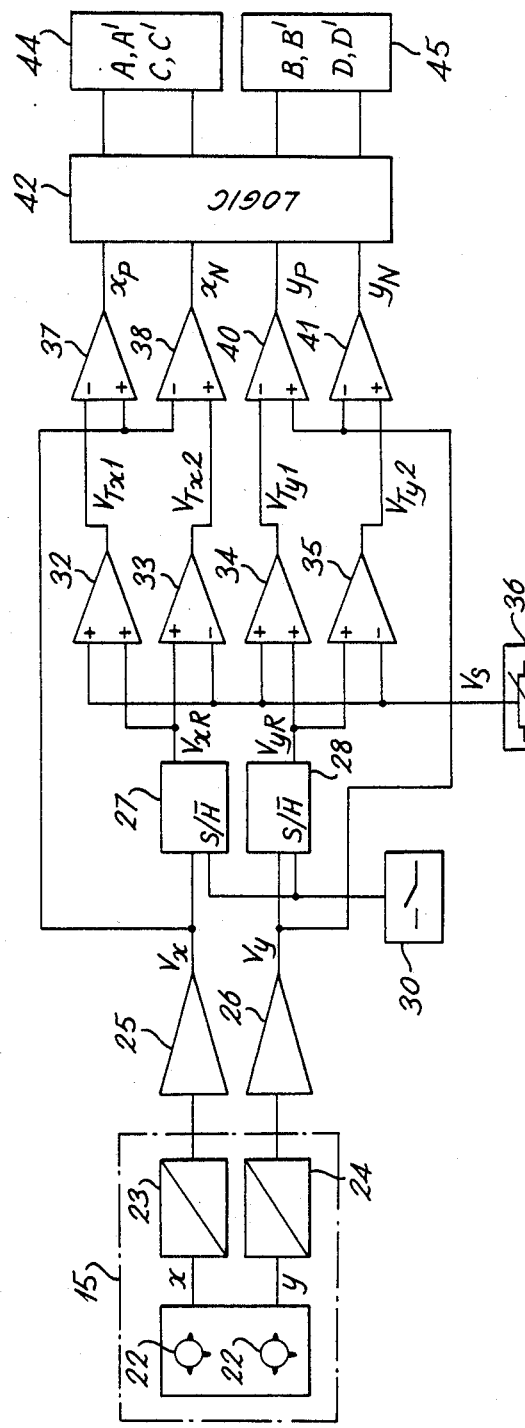
FIG. 3 is a block diagram of an alignment indicator according to the invention.

FIG. 3 shows an analogue implementation of one way in which signal processing can be provided. The housing 15 contains uniaxial electrolytic tilt sensors 22 as the "electronic spirit levels". These sensors are connected to sensor modules 23 and 24 which provide excitation to the sensors and give a voltage output proportional to tilt from vertical. These voltages are connected as input signals to signal conditioning amplifiers 25 and 26, respectively, which amplify the sensor module outputs and apply an offset to them.

Sample and hold circuits 27 and 28 are used to establish the selected axis mentioned above. When the cutter is in the position to start preparation, a footswitch 30 is operated to hold the current values $V_x$ and $V_y$ (the outputs of amplifiers 25 and 26, respectively), as signals $V_{xR}$ and $V_{yR}$. Only tilt greater than a certain threshold is indicated by the LEDs and this threshold is established by means of summing amplifiers 32 to 35 and a sensitivity circuit 36 illustrated as an adjustable potentiometer with an output $V_S$. Plus and minus signs at the inputs to the amplifiers 32 to 35 indicate whether the output signals from the sample and hold circuits are added to or subtracted from the signal $V_S$ in forming four threshold signals as given below:

$$V_{Tx1} = V_{xR} + V_s$$

$$V_{Tx2} = V_{xR} - V_s$$

$$V_{Ty1} = V_{yR} + V_s$$

$$V_{Ty2} = V_{yR} - V_s$$

The $V_x$ tilt signal from the amplifier 25 is applied to two comparators 37 and 38 which receive respective threshold signals from summing amplifiers 32 and 33. As a result "high" signals $x_P$ and $x_N$ appear at the output of comparators 37 and 38 when a signal greater than threshold in the positive and negative senses, respectively, appears at the output of comparators 37 and 38. These signals and similar signals $y_P$ and $y_N$ appearing at the output of comparators 40 and 41 are used in a logic circuit 42, described in more detail below, to control the LEDs in two groups indicated by boxes 44 and 45.

Figure 4:
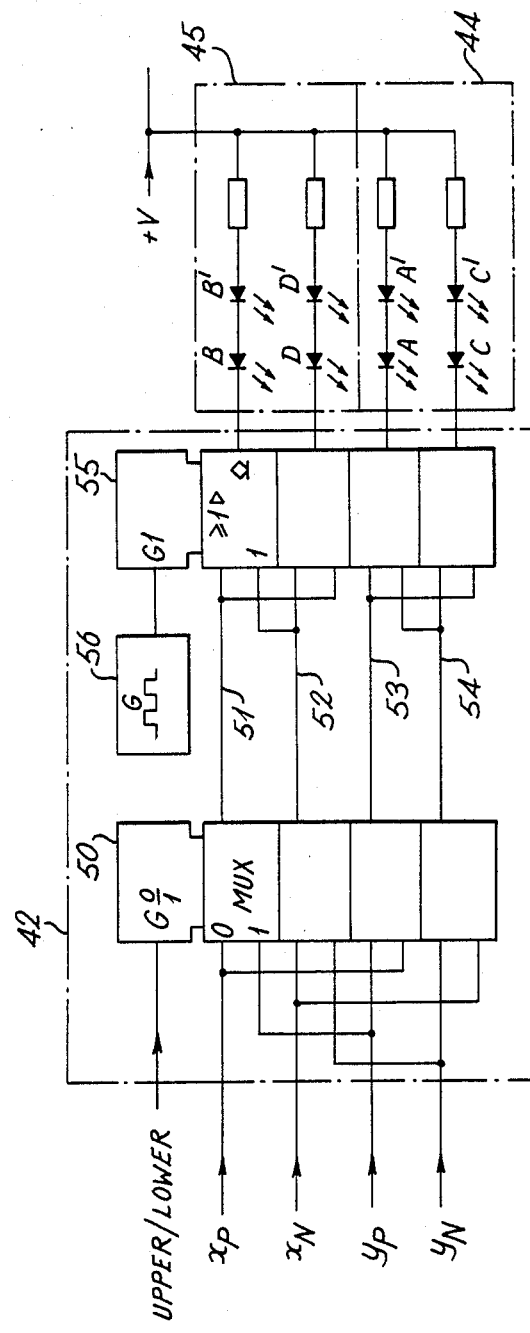
FIG. 4 is a diagram of logic which may be used as part of FIG. 3.

The logic circuit 42 is shown in FIG. 4 which employs the logic symbols defined by the International Electrotechnical Commission (IEC), Geneva, and described in IEC publication 617:12, Binary Logic Elements. A multiplexer element 50 receives an upper/(inverted) lower signal from a switch (not shown) operated by the practitioner to indicate whether he is working on the upper or lower jaw. If preparation is to be on the upper jaw the upper section (as illustrated) of the multiplexer 50 receives a "high" signal and the four lower sections of the multiplexer 50 are gated to pass their lower input signals to their outputs; that is inputs $x_P$ and $x_N$ are gated onto connections 53 and 54, respectively, while signals $y_P$ and $y_N$ are gated onto connections 51 and 52. If preparation is to be on the lower jaw signals $x_P$ and $x_N$ reach conductors 51 and 52, respectively, and signals $y_P$ and $y_N$ reach conductors 53 and 54, respectively.

The conductors 51 to 54 are connected to an OR gate assembly 55 receiving common clock signal from a clock circuit 56. To illustrate operation consider the situation where there is tilt above threshold in the positive x direction and the negative y direction, preparation being carried out on the upper jaw; that is conductors 52 and 53 are "high" while conductors 51 and 54 are "low". According to the IEC definitions the symbol "G1" means that only those terminals marked 1 are gated and also according to the definitions only the section below the upper control section contains designations while the other sections are left blank but are assumed to have the same designations. Thus the high signal on conductor 52 operates the LEDs D and D' continuously while LEDs B and B' are flashed at the clock rate by virtue of the gating. Similarly the high condition of the conductor 53 operates the LEDs A and A' continuously while flashing the LEDs C and C'. As can be seen LED operation is in accordance with the code described above. The operation of the gate assembly 55 to give the illuminated light code for the remaining combinations of signals on the conductors 51 to 54 will be apparent from the above example.

Figure 5:
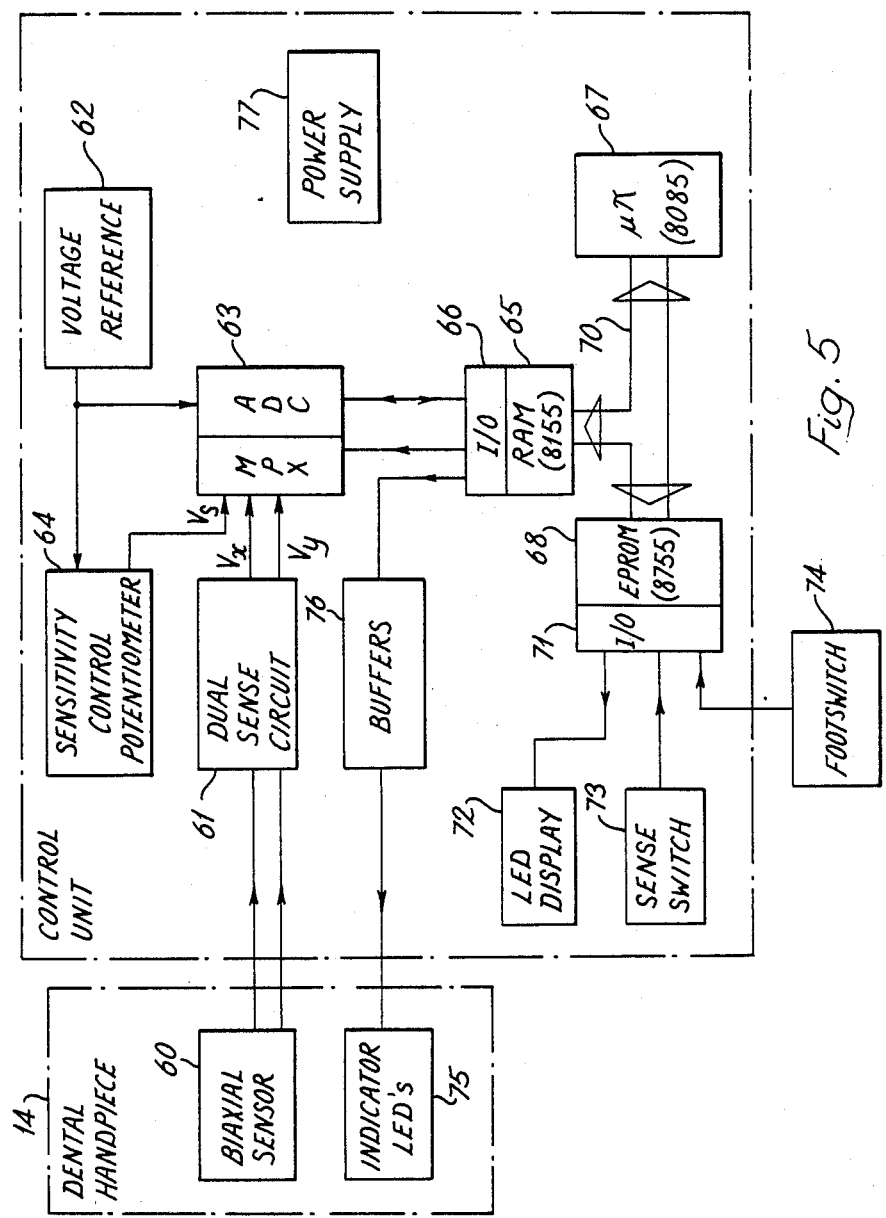
FIG. 5 is a block diagram of another alignment indicator according to the invention employing a microprocessor.

As an alternative to the circuits of FIGS. 3 and 4 a microprocessor implementation is shown in FIG. 5. In this arrangement the uniaxial sensors are replaced by a biaxial sensor 60 with two outputs corresponding to x and y tilt and a dual sense circuit 61 provides the output signals $V_x$ and $V_y$. A circuit 62 provides a reference voltage for a multiplexed analogue-to-digital converter 63 and a sensitivity control potentiometer 64. The three voltages $V_s$, $V_x$ and $V_y$ are applied in digital form to a random access memory (RAM) 65 by the multiplexed analogue-to-digital converter 63 through input/output circuits 66 under the control of a microprocessor 67. An erasable, programmable read-only memory (EPROM) 68 contains the control program for microprocessor 67 and is connected thereto and to the RAM 65 by a system bus 70. The EPROM 68 is connected by way of an input/output circuit 71 to an LED display 72 which indicates the sensitivity of the circuit; that is the values of the thresholds as set by the control potentiometer 64. In addition the I/O circuit 71 is connected to a sense switch 73 for operation to indicate preparation of a tooth in the upper or lower jaw and a footswitch 74 which is operated when the cutter 10 is in position ready for the start of preparation. The LEDs A to D' are indicated by a box 75 which is connected by way of buffer circuits 76 to the I/O circuit 66. The circuit of FIG. 5 is powered by a power supply unit 77 which is a medical grade mains power supply.

The following circuits are suitable for the microprocessor 67, the RAM 65 and the EPROM 68, respectively, types 8085, 8155 and 8755.

Figure 6:
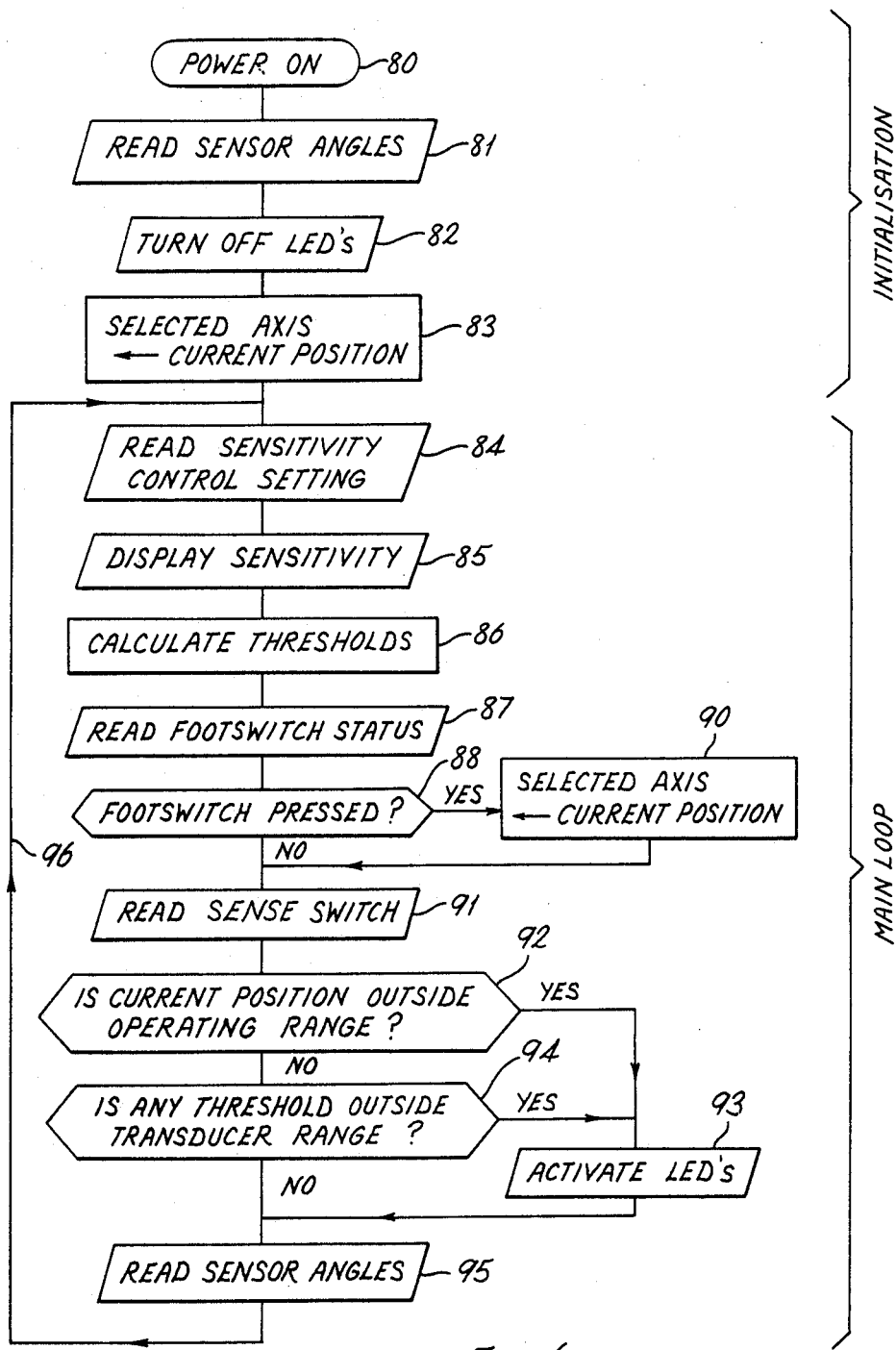
FIG. 6 is a flow chart for the alignment indicator of FIG. 5.

The microprocessor 67 operates according to the flow chart of FIG. 6. On power-on (operation 80) initialisation commences and the voltages $V_x$ and $V_y$ are read into the RAM 65 in an operation 81, the LEDs of boxes 72 and 75 are turned off (operation 82) and the current position of the dental handpiece is set to define the selected axis (operation 83).

The main loop of the flow chart is then entered in operation 84 where the sensitivity control setting is read as set by the dentist using the potentiometer 64. An operation 85 displays this setting using a table in the EPROM 68 and the LEDs of the box 72. Further an operation 86 is carried out to calculate the thresholds.

An operation 87 reads the state of the footswitch and a test 88 indicates whether the footswitch is pressed. If so the selected axis is set to represent the current position of the cutter 10 in an operation 90 using the current digitised values of $V_x$ and $V_y$ held by the RAM 65. Following the operation 90 or if the footswitch is not pressed the test 88, the sense switch 73 is read (operation 91) and the test 92 carried out to determine whether tilt in either direction exceeds threshold. If so the appropriate LEDs on the handpiece are operated in an operation 93, but if not a test 94 is carried out to determine whether any threshold set is outside the transducer range; that is the range over which the biaxial sensor 60 and the dual sense circuit 61 provide a substantially linear signal representative of tilt angle. If so the appropriate LEDs on the handpiece are operated in an operation 93 but if not and if all thresholds are inside the transducer range the sensor angles $V_x$ and $V_y$ are read in operation 95 and then the main loop is repeated as indicated by the line 96.

As an alternative to the microprocessor implementation a micro-controller may be used where a central processing unit, memory, input/output, multiplexer and an anlogue-to-digital converter are integrated into one package. A similar flow chart is used.

Significant movement of the patient's upper jaw during preparation is not likely to occur because the back of the head is usually supported, but movement of the lower jaw may occasionally take place. Where this problem arises a lower jaw rest may be used or two movement sensors (one for each of two axes at right angles) in a single housing may be attached to the lower jaw, for example by being clipped to a tooth. When the dentist is ready to start work and is holding the cutter in the starting position, the current $V_x$ signal, the current $V_g$ signal and jaw sensor signals are stored. The apparatus is not constructed to give tilt indicating signals but only to provide a warning if the sum of the deviations of the signals from their respective stored values exceeds a predetermined value. The dentist then rests the drill against the surface where preparation started and resets the selected axis by pressing the footswitch. If the error is the dentist's then the selected axis will be much as before but if the lower jaw has moved a new axis will be selected.

The invention may be put into practice in many other ways than those specifically described. The LED displays may, for example, be replaced by fibre optics or liquid crystal displays and for the handpiece display the LEDs or alternatives may be either built into a specially constructed handpiece or positioned on a mounting which is clipped to a conventional handpiece.

A computer generated vocal output may be used in addition to, or as an alternative for, the handpiece display or audio signals using, for example high or low pitches for the two axes and continuous or interrupted sounding may be used. A single audio signal which indicates unacceptable alignment error may be sufficient and even a tactile warning may be suitable.

The handpiece display can be considered as feedback given to a dentist and it may be given without directional information by a single lamp or by modulating the intensity of a main optical fibre built into the handpiece. The colour applied to the main fibre optic may be modulated to give directional information.

Alternatives to the uniaxial and biaxial sensors include sensitive pendulum inclinometers, non-electrolytic capacitive transducers, resistive transducers and magnetic field sensing coils in an externally generated field.

In some implementations it may be useful to provide an indication of angular position in a plane normal to the selected axis. A magnetic compass with electrical output may be used for this purpose and the information displayed by liquid-crystal display-arrows on the handpiece.

The footswitch may be replaced by a manually operated switch on the handpiece or by voice recognition circuits.

It is expected that eventually the signal processing circuits will be miniaturized and mounted on the handpiece with battery power.

The sensitivity control may be mounted on the handpiece both in the miniaturized and other versions while in the latter case the signal processing circuits remain in a separate unit.

A mercury tilt switch may be attached to the handpiece and used as an alternative to the manually operated sense switch to indicate work on the upper or lower jaw.

We claim:

1. A parallel alignment indicator for a dental handpiece, comprising:
   angle-indicator means for generating electrical angle signals representative of an angular orientation of an axis of a cutter held, in operation, by a dental handpiece;
   setting means for setting electrical reference signals representing a position of a pre-selected axis; and
   warning means arranged to generate a warning when a relationship between the electrical angle signals and the electrical reference signals falls outside predetermined limits.

2. An alignment indicator according to claim 1 wherein the warning means includes visual-indicator means constructed to give a visual warning and to ensure that any said visual warning given is within the field of view of the operator of the dental handpiece when observing the cutter whatever the position of the handpiece in a patient's mouth.

3. An alignment indicator according to claim 2 further including means for generating coded signals indicating when the angle between the cutter axis and the pre-selected axis is greater than an adjustable threshold angle.

4. An alignment indicator according to claim 3 wherein the visual-indicator means comprises a plurality of light sources for displaying the coded signals so mounted, in operation, on the handpiece that, wherever the handpiece is positioned when a tooth is being cut, sufficient of the sources can be seen by the operator controlling cutting for the coded signals to be understood.

5. An alignment indicator according to claim 4 wherein the coded signals specify the direction of tilt of the handpiece.

6. An alignment indicator according to claim 1 wherein the angle-indicator means is constructed to ensure that the said angle signals are representative of the amount of deviation from a reference axis, the setting means includes storage means for storing the angle signals when the handpiece has been positioned in a chosen position related to the pre-selected axis, and the warning means includes means for comparing the current angle signals with signals derived from the stored signals and a predetermined threshold signal.

* * * * *